United States Patent [19]

Webster

[11] 4,389,782

[45] Jun. 28, 1983

[54] DETERMINATION OF THE EXTENT OF A DECUBITUS ULCER

[75] Inventor: David F. Webster, Santa Rosa, Calif.

[73] Assignee: Nomode Incorporated, Santa Rosa, Calif.

[21] Appl. No.: 352,939

[22] Filed: Feb. 26, 1982

Related U.S. Application Data

[63] Continuation of Ser. No. 113,051, Jan. 17, 1980, abandoned.

[51] Int. Cl.³ .................................................. G01B 3/00
[52] U.S. Cl. .................................... 33/1 BB; 33/1 R; 33/174 D; 128/736
[58] Field of Search .............. 33/1 R, 1 B, 1 BB, 1 C, 33/189, 174 A, 174 B, 200, 293, 431, 174 D; 128/736, 774; 40/307, 2 G

[56] References Cited

U.S. PATENT DOCUMENTS

| | | | |
|---|---|---|---|
| 2,190,582 | 2/1940 | Wolf | 33/174 A |
| 2,648,924 | 8/1953 | Brewster | 283/18 X |
| 2,764,817 | 10/1956 | Schwartz | 33/189 |
| 3,312,365 | 4/1967 | Balint | 40/307 X |
| 3,484,976 | 12/1969 | Shea | 283/19 X |
| 3,528,077 | 9/1970 | Seiden | 33/1 B |
| 3,594,463 | 7/1971 | Saurino | 128/156 |
| 3,769,071 | 10/1973 | Trancik | 128/156 |
| 3,816,923 | 6/1974 | Habermeier | 33/1 BB |
| 3,819,490 | 6/1974 | Klingstrom et al. | 33/1 BB |
| 4,131,998 | 1/1979 | Spears | 127/774 |
| 4,159,586 | 7/1979 | Blum | 283/21 |
| 4,190,058 | 2/1980 | Sagi | 128/736 |
| 4,197,944 | 4/1980 | Catlin | 128/736 |

Primary Examiner—William D. Martin, Jr.

[57] ABSTRACT

A decubitus ulcer, more commonly referred to by a layman as a bedsore, is brought on by continued pressure of a body area where the overlying skin in the area is poorly padded. The most vulnerable areas are the elbows, tailbone, hips, knees, ankles, heels and shoulder blades. The only evaluation of the existence of such an ulcer is solely by record keeping of "eyeball" evaluation.

3 Claims, 8 Drawing Figures

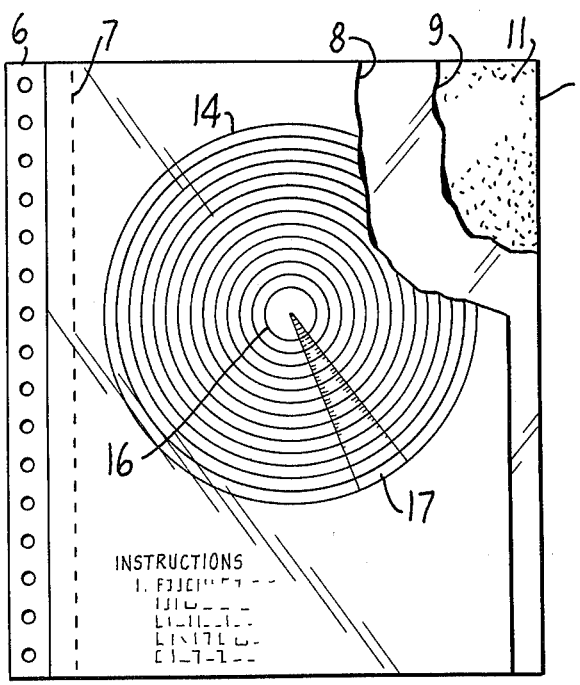
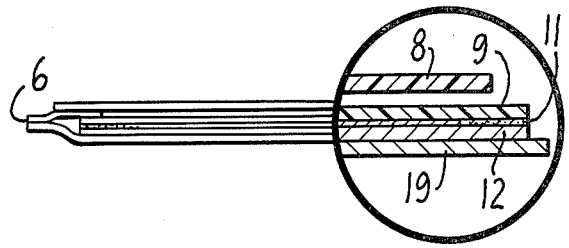
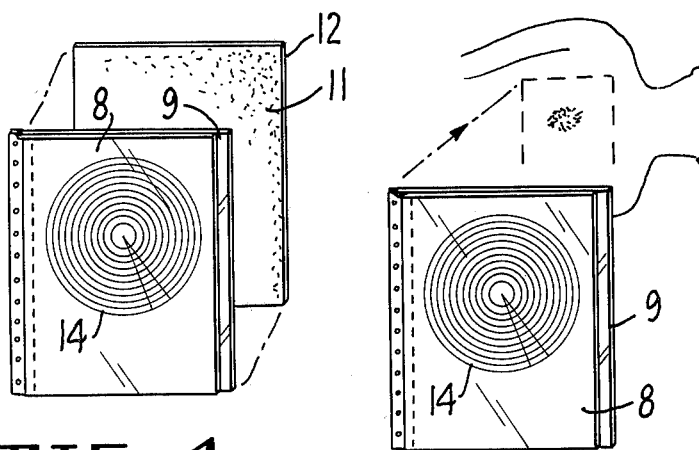
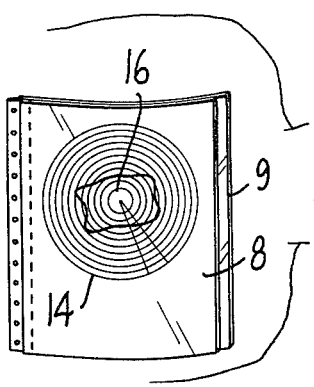
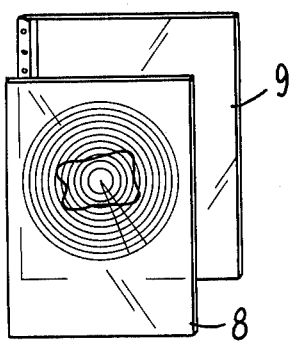
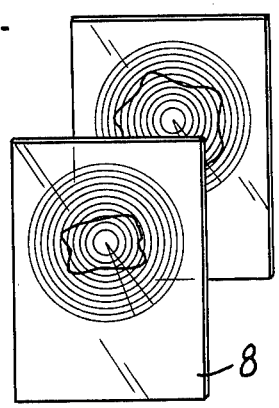

DETERMINATION OF THE EXTENT OF A DECUBITUS ULCER

This is a continuation, of application Ser. No. 113,051, filed Jan. 17, 1980, now abandoned.

BACKGROUND OF THE INVENTION

An early indication of skin breakdown or potential decubitus ulcer areas is provided by a reddening of the skin covering pressure areas that remain in constant contact against a hard surface such as those of a mattress or a bed sheet. Frequent contact between those areas of the human body on mattress coverings such as sheets or other materials will cause the skin to redden resulting in skin breakdown. Later stages of such ulceration results in a raw or purplish and impaired circulation condition. When inspection during bathing or turning of a patient indicates tht any of the above areas are subject to this most difficult near ulceration problem, the reddened or chaffed skin may breakdown on extremely short notice.

The existence of decubitus ulcers is not solely limited to geriatric patients. Patients who are required to remain in a fixed condition due to bone fracture, such as traction, may develop decubitus ulcers at an early age if confined to a hospital bed.

Frequently patients are transferred to extended care facilities from an acute hospital. The device of this invention enables an extended care facility upon inspection of an incoming patient to show proof of the then condition of the patient upon admittance from an acute hospital, thus preventing the citation frequently issued by a department of health.

SUMMARY OF THE INVENTION

It is in general the broad object of the present invention to provide a device which enables the extent of a decubitus ulcer to be ascertained with a permanent record for comparison from day to day to show either improvement or further deterioration.

The device comprises a peel-off backing of a germicidally treated material which is adhered to an intermediate clear see-through sheet and hingedly attached along one edge to an overlying clear see-through sheet imprinted with a measuring ring and sector.

BRIEF DESCRIPTION OF THE DRAWINGS

FIG. 1 is a plan view of a completed form of the device.

FIGS. 2 and 3 are, respectively, end views of two embodiments of the device shown in FIG. 1 and showing enlarged sectional views of their construction.

FIG. 4 is a perspective view showing the device ready for use with the back sheet removed.

FIG. 5 shows the device being positioned over the patient such that the decubitus ulcer will be centered in the measuring ring.

FIG. 6 is a view showing application of the device with the attendant having drawn an outline of the ulcerated area.

FIG. 7 is a view similar to FIG. 6 but with the intermediate barrier sheet removed.

FIG. 8 shows the comparison of one record with respect to an earlier record showing a reduction in the extent of the ulcer; this record and its previous record are filed in the patient's chart.

DESCRIPTION OF THE PREFERRED EMBODIMENT

Referring to the drawings, the device of the present invention includes a plurality of sheets of different materials secured along the lefthand margin 6 and foldable over fold line 7. These include a transparent outer sheet 8 positioned over a barrier sheet 9 which extends over an adhesive coated area 11 on the base sheet 12. Included with the adhesive is a germicide such as a quaternary ammonium salt with or without a mercurial additive which protects the patient contacting side of the barrier sheet 9. The outer sheet 8 includes a plurality of concentric measuring rings 14 spaced about a central eye 16. The distance between the concentric circles is generally of the order of one-eighth of an inch. A sector 17 may also be included in which the color density of the ulcer may be noted. The apex of sector 17 is preferably printed with a red color while the area in the succeeding rings in the sector 17 includes red dots. This enables a person utilizing the device to apply red ink in the ring or rings in the area affected. Each of rings 14 is printed in a blue color. The eye 16 is usually made one-half inch in diameter while the outer rings are spaced an eighth of an inch apart. The coloring of sector 17 enables a comparison to be made with the color density of the ulcerated area.

As shown in FIGS. 2 and 3, the base sheet 12 may form the rigid member of the assembly (as in FIG. 2) or may be augmented by a separate stiffener sheet 19 (as shown in FIG. 3). The structure of FIG. 3 allows adhesive coated sheet 12 and barrier sheet 9 to be subassembled prior to assembly with sheet 8.

In use, one removes the backing sheet 12 as is shown in FIG. 4. The resulting structure in planar form is then placed with the center of the eye over the central portion of the skin lesion as shown in FIG. 5. The attendant then draws an outline of the lesion on the top sheet 8 as is shown in FIG. 6. Barrier sheet 9 is then removed and discarded, leaving the uninfected upper sheet 8 which may now safely be handled and filed. The reddened area may be measured from the outer ring of the ulcer to the healthy skin surface. The skin improvement or breakdown may be established by comparing the areas of FIGS. 7 and 8. For example, the eye of the ring plus rings 1 and 2 are decubitus areas while rings 3 and 4 are reddened areas subject to expansion or retraction of the decubitus area as is shown by a comparison of reduction in this area between FIGS. 7 and 8. The backing provided by bottom sheet 12 should be on a material which is not hygroscopic for, if it is, it will tend to curl into a rolled form because it will pick up moisture from the atmosphere.

I claim:

1. A device for recording the extent of a decubitus ulcer on the skin of a patient comprising a transparent barrier sheet having a top face and a bottom face with an adhesive on the bottom face for securing the barrier sheet in position over an ulcerated region on a patient, and a transparent outer sheet removably positioned over the top face of the barrier sheet, said outer sheet having a plurality of spaced concentric rings arranged concentrically about a central eye which is positioned in use over the central portion of the skin lesion provided by a decubitus ulcer.

2. A device as in claim 1 wherein the bottom face of the transparent barrier sheet is secured to an adhesive coated face on a base sheet.

3. A device for recording the extent of a decubitus ulcer on the skin of a patient comprising a transparent barrier sheet having a top face and a bottom face with an adhesive on the bottom face for securing the barrier sheet in position over an ulcerated region on a patient, and a transparent outer sheet positioned over the top face of the barrier sheet, said outer sheet having a plurality of spaced concentric circles concentrically positioned about a central eye which is positioned over a central portion of a skin lesion provided by a decubitus ulcer when the bottom face of the attached barrier sheet is attached to the skin of a patient, said transparent outer sheet being separable from the bottom sheet to permit discard of the barrier sheet and record use of the outer sheet.

* * * * *